(12) United States Patent
Wu

(10) Patent No.: US 6,291,656 B1
(45) Date of Patent: Sep. 18, 2001

(54) TRICYCLIC ERYTHROMYCIN DERIVATIVES

(75) Inventor: Yong-Jin Wu, East Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/341,888

(22) PCT Filed: Oct. 8, 1998

(86) PCT No.: PCT/IB98/01559

§ 371 Date: Jul. 15, 1999

§ 102(e) Date: Jul. 15, 1999

(87) PCT Pub. No.: WO99/21865

PCT Pub. Date: May 6, 1999

Related U.S. Application Data

(60) Provisional application No. 60/063,161, filed on Oct. 29, 1997.

(51) Int. Cl.[7] .................................................. C07H 17/08
(52) U.S. Cl. ............................ 536/7.4; 514/29; 536/18.5
(58) Field of Search ........................... 536/7.2, 7.4, 18.5; 514/29

(56) References Cited

FOREIGN PATENT DOCUMENTS

| 0638585 | 2/1995 | (EP) . |
|---|---|---|
| 9717356 | 5/1997 | (WO) . |

*Primary Examiner*—Elli Peselev
(74) *Attorney, Agent, or Firm*—Peter C. Richardson; Paul H. Ginsburg; Bryan C. Zielinski

(57) ABSTRACT

The invention relates to compounds of the formula I

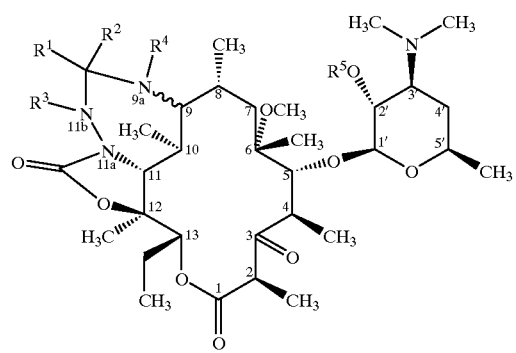

and to pharmaceutically acceptable salts thereof, wherein $R^1$, $R^2$, $R^3$, $R^4$ and $R^5$ are as defined herein. The invention also relates to pharmaceutical compositions containing the compounds of formula I, methods of using said compounds of formula I in the treatment of infections, and methods of preparing said compounds of formula I.

12 Claims, No Drawings

TRICYCLIC ERYTHROMYCIN DERIVATIVES

This application, filed under 35 U.S.C. §371, is a national stage application of PCT International application number PCT/IB98/01559, filed Oct. 8, 1998, which claims the benefit of U.S. provisional application No. 60/063,161, filed Oct. 29, 1997.

BACKGROUND OF THE INVENTION

This invention relates to novel tricyclic erythromycin derivatives. The compounds of this invention are useful as antibiotic agents in mammals, including man, as well as in fish and birds. The compounds of the present invention are broad-spectrum macrolide antibiotics that are effective against infections caused by certain gram-positive and gram-negative bacteria as well as protozoa. Various derivatives of erythromycin A useful as antibiotic agents are referred to in U.S. patent application Ser. No. 60/049,349, filed Jun. 11, 1997, and U.S. application Ser. No. 60/046,150, filed May 9, 1997, both of which are incorporated herein by reference in their entirety, and in U.S. patent application Ser. No. 60/063676, entitled "9-Amino-3-Keto Erythromycin Derivatives", (Yong-Jin Wu), filed Oct. 29, 1997, which is incorporated herein by reference in its entirety.

SUMMARY OF THE INVENTION

The present invention relates to compounds of the formula I

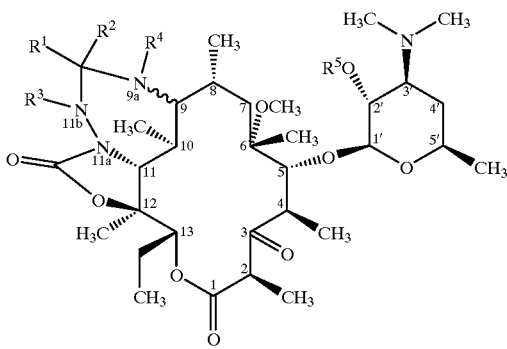

I and pharmaceutically acceptable salts thereof, wherein:
each $R^1$ and $R^2$ is independently selected from H and $C_1$–$C_2$ alkyl, wherein one or two carbons of said alkyl are optionally replaced by a heteroatom selected from O, S and N, and are optionally substituted by 1 to 3 substituents selected from the group consisting of —C(O)$OR^6$, —$OR^6$, $C_1$–$C_{10}$ alkanoyl, halo, nitro, cyano, $R^6$, $R^8$, —$NR^6R^7$, —$SR^6$, —$SOR^6$, —$SO_2R^6$ and —$SO_2NR^6R^7$.

$R^3$ is H, $R^7$, $C(O)R^7$, $C(O)R^8$, $C(O)OR^7$, $C(O)OR^8$, or $(CR^6R^7)_mR^8$, wherein m is an integer ranging from 0 to 6;

$R^4$ is H or $C_1$–$C_{12}$ alkyl, wherein one or two carbons of said alkyl are optionally replaced by a heteroatom selected from O, S and N, and are optionally substituted by 1 to 3 substituents selected from the group consisting of —C(O)$OR^6$, —$OR^6$, $C_1$–$C_{10}$ alkanoyl, halo, nitro, cyano, $R^6$, $R^8$, —$NR^6R^7$, —$SR^6$, —$SOR^6$, —$SO_2R^6$ and —$SO_2NR^6R^7$;

$R^5$ is H, —C(O)$R^8$ or $C_1$–$C_{18}$ alkanoyl, wherein in the alkyl portion of said alkanoyl one or two carbons optionally may be replaced by a heteroatom selected from O, S and N;

each $R^6$ and $R^7$ is independently selected from H and $C_1$–$C_{12}$ alkyl; and each $R^8$ is independently a 4–10 membered heterocyclic or $C_6$–$C_{10}$ aryl, wherein said heterocycyclic and aryl groups are optionally substituted by 1 to 3 substituents independently selected from the group consisting of 4–10 membered heterocyclic, $C_6$–$C_{10}$ aryl, —NHC(O)$R^6$, —NHC(O)$NR^6R^7$, —C(O)$OR^6$, —$OR^6$, —C(O)$R^6$, halo, nitro, cyano, $R^6$, —$NR^6R^7$, —$SR^6$, —$S(O)R^6$, —$SO_2R^6$ and —$SO_2NR^6R^7$.

More specific embodiments of the invention include compounds of claim 1 wherein $R^5$ is H.

More specific embodiments of the invention include compounds of claim 1 wherein $R^1$ is H.

More specific embodiments of the invention include compounds of claim 1 wherein each of $R^1$ and $R^2$ is H.

More specific embodiments of the invention include compounds of claim 1 wherein each of $R^1$ and $R^2$ is H and wherein $R^4$ is H, methyl, ethyl, isopropyl, propyl, or cyclopropyl.

More specific embodiments of the invention include compounds of claim 1 wherein $R^3$ is $(CH_2)_mR^8$, m is an integer ranging from 0 to 6 and $R^8$ is as defined in formula I.

More specific embodiments of the invention include compounds of claim 1 wherein $R^3$ is $(CH_2)_3R^8$.

Specific embodiments of $R^8$ include quinolin-4-yl, 4-phenyl-1-imidazol-1-yl, imidazo(4,5-b)pyridin-3-yl, or 4-pyridin-3-yl-imidazol-1-yl.

Examples of preferred compounds of the present invention include a compound of formula I selected from the group consisting of:
the compound of formula I wherein each of $R^1$, $R^2$, $R^4$ and $R^5$ is H and $R^3$ is 3-quinolin-4-yl-propyl;
the compound of formula I wherein each of $R^1$, $R^2$ and $R^5$ is H, $R^4$ is methyl and $R^3$ is 3-quinolin-4-yl-propyl;
the compound of formula I wherein each of $R^1$, $R^2$ and $R^5$ is H, $R^4$ is ethyl and $R^3$ is 3-quinolin-4-yl-propyl;
the compound of formula I wherein each of $R^1$, $R^2$ and $R^5$ is H, $R^4$ is propyl and $R^3$ is 3-quinolin-4-yl-propyl;
the compound of formula I wherein each of $R^1$, $R^2$ and $R^5$ is H, $R^4$ is isopropyl and $R^3$ is 3-quinolin-4-yl-propyl;
the compound of formula I wherein each of $R^1$, $R^2$ and $R^5$ is H, $R^4$ is cyclopropyl and $R^3$ is 3-quinolin-4-yl-propyl;
the compound of formula I wherein each of $R^1$, $R^2$, $R^4$ and $R^5$ is H and $R^3$ is 3-(7-methoxy-quinolin-4-yl)-propyl;
the compound of formula I wherein each of $R^1$, $R^2$ and $R^5$ is H, $R^4$ is methyl and $R^3$ is 3-(7-methoxy-quinolin-4-yl)-propyl;
the compound of formula I wherein each of $R^1$, $R^2$ and $R^5$ is H, $R^4$ is ethyl and $R^3$ is 3-(7-methoxy-quinolin-4-yl)-propyl;
the compound of formula I wherein each of $R^1$, $R^2$ and $R^5$ is H, $R^4$ is propyl and $R^3$ is 3-(7-methoxy-quinolin-4-yl)-propyl;
the compound of formula I wherein each of $R^1$, $R^2$ and $R^5$ is H, $R^4$ is isopropyl and $R^3$ is 3-(7-methoxy-quinolin-4-yl)-propyl;

the compound of formula I wherein each of $R^1$, $R^2$ and $R^5$ is H, $R^4$ is cyclopropyl and $R^3$ is 3-(7-methoxy-quinolin-4-yl)-propyl;

the compound of formula I wherein each of $R^1$, $R^2$, $R^4$ and $R^5$ is H and $R^3$ is 3-(4-phenyl-imidazol-1-yl)-propyl;

the compound of formula I wherein each of $R^1$, $R^2$ and $R^5$ is H, $R^4$ is $CH_3$ and $R^3$ is 3-(4-phenyl-imidazol-1-yl)-propyl;

the compound of formula I wherein each of $R^1$, $R^2$ and $R^5$ is H, $R^4$ is ethyl and $R^3$ is 3-(4-phenyl-imidazol-1-yl)-propyl;

the compound of formula I wherein each of $R^1$, $R^2$ and $R^5$ is H, $R^4$ is propyl and $R^3$ is 3-(4-phenyl-imidazol-1-yl)-propyl;

the compound of formula I wherein each of $R^1$, $R^2$ and $R^5$ is H, $R^4$ is isopropyl and $R^3$ is 3-(4-phenyl-imidazol-1-yl)-propyl;

the compound of formula I wherein each of $R^1$, $R^2$ and $R^5$ is H, $R^4$ is cyclopropyl and $R^3$ is 3-(4-phenyl-imidazol-1-yl)-propyl;

the compound of formula I wherein each of $R^1$, $R^2$, $R^4$ and $R^5$ is H and $R^3$ is 3-(4-pyridin-3-yl-imidazol-1-yl)-propyl;

the compound of formula I wherein each of $R^1$, $R^2$ and $R^5$ is H, $R^4$ is $CH_3$ and $R^3$ is 3-(4-pyridin-3-yl-imidazol-1-yl)-propyl;

the compound of formula I wherein each of $R^1$, $R^2$ and $R^5$ is H, $R^4$ is ethyl and $R^3$ is 3-(4-pyridin-3-yl-imidazol-1-yl)-propyl;

the compound of formula I wherein each of $R^1$, $R^2$ and $R^5$ is H, $R^4$ is propyl and $R^3$ is 3-(4-pyridin-3-yl-imidazol-1-yl)-propyl;

the compound of formula I wherein each of $R^1$, $R^2$ and $R^5$ is H, $R^4$ is isopropyl and $R^3$ is 3-(4-pyridin-3-yl-imidazol-1-yl)-propyl;

the compound of formula I wherein each of $R^1$, $R^2$ and $R^5$ is H, $R^4$ is cyclopropyl and $R^3$ is 3(4-pyridin-3-yl-imidazol-1-yl)-propyl;

the compound of formula I wherein each of $R^1$, $R^2$, $R^4$ and $R^5$ is H and $R^3$ is 3-imidazo(4,5-b)pyridin-3-yl-propyl;

the compound of formula I wherein each of $R^1$, $R^2$ and $R^5$ is H, $R^4$ is $CH_3$ and $R^3$ is 3-imidazo(4,5-b)pyridin-3-yl-propyl;

the compound of formula I wherein each of $R^1$, $R^2$ and $R^5$ is H, $R^4$ is ethyl and $R^3$ is 3-imidazo(4,5-b)pyridin-3-yl-propyl;

the compound of formula I wherein each of $R^1$, $R^2$ and $R^5$ is H, $R^4$ is propyl and $R^3$ is 3-imidazo(4,5-b)pyridin-3-yl-propyl;

the compound of formula I wherein each of $R^1$, $R^2$ and $R^5$ is H, $R^4$ is isopropyl and $R^3$ is 3-imidazo(4,5-b)pyridin-3-yl-propyl;

the compound of formula I wherein each of $R^1$, $R^2$ and $R^5$ is H, $R^4$ is cyclopropyl and $R^3$ is 3-imidazo(4,5-b)pyridin-3-yl-propyl;

the compound of formula I wherein each of $R^1$, $R^2$, $R^4$ and $R^5$ is H and $R^3$ is 3-pyridin-4-yl-propyl;

the compound of formula I wherein each of R, $R^2$ and $R^5$ is H, $R^4$ is $CH_3$ and $R^3$ is 3-pyridin-4-yl-propyl;

the compound of formula I wherein each of $R^1$, $R^2$ and $R^5$ is H, $R^4$ is ethyl and $R^3$ is 3-pyridin-4-yl-propyl;

the compound of formula I wherein each of $R^1$, $R^2$ and $R^5$ is H, $R^4$ is propyl and $R^3$ is 3-pyridin-4-yl-propyl;

the compound of formula I wherein each of $R^1$, $R^2$ and $R^5$ is H, $R^4$ is isopropyl and $R^3$ is 3-pyridin-4-yl-propyl;

the compound of formula I wherein each of $R^1$, $R^2$ and $R^5$ is H, $R^4$ is cyclopropyl and $R^3$ is 3-pyridin-4-yl-propyl;

the compound of formula I wherein each of $R^1$, $R^2$, $R^4$ and $R^5$ is H and $R^3$ is 3-phenylpropyl;

the compound of formula I wherein each of $R^1$, $R^2$ and $R^5$ is H, $R^4$ is methyl and $R^3$ is 3-phenylpropyl;

the compound of formula I wherein each of $R^1$, $R^2$ and $R^5$ is H, $R^4$ is ethyl and $R^3$ is 3-phenylpropyl;

the compound of formula I wherein each of $R^1$, $R^2$ and $R^5$ is H, $R^4$ is propyl and $R^3$ is 3-phenylpropyl;

the compound of formula I wherein each of $R^1$, $R^2$ and $R^5$ is H, $R^4$ is isopropyl and $R^3$ is 3-phenylpropyl; and the pharmaceutically acceptable salts of the foregoing compounds.

The invention also relates to a pharmaceutical composition for the treatment of an infection in a mammal, fish or bird which comprises a therapeutically effective amount of a compound of claim 1 and a pharmaceutically acceptable carrier.

The invention also relates to a method of treating an infection in a mammal, fish, or bird which comprises administering to said mammal, fish, or bird a therapeutically effective amount of a compound of claim 1.

The invention also relates to a method of preparing a compound of the formula I and pharmaceutically acceptable salts thereof, wherein:

each $R^1$ and $R^2$ is independently selected from H and $C_1$–$C_{12}$ alkyl, wherein one or two carbons of said alkyl are optionally replaced by a heteroatom selected from O, S and N, and are optionally substituted by 1 to 3 substituents selected from the group consisting of —C(O)$OR^6$, —$OR^6$, $C_1$–$C_{10}$ alkanoyl, halo, nitro, cyano, $R^6$, —$NR^6R^7$, —$SR^6$, —$SOR^6$, —$SO_2R^6$ and —$SO_2NR^6R^7$;

$R^3$ is H, $R^7$, C(O)$R^7$, C(O)$R^8$, C(O)$OR^7$, C(O)$OR^8$, or $(CR^6R^7)_m R^8$, wherein m is an integer ranging from 0 to 6;

$R^4$ is H or $C_1$–$C_{12}$ alkyl, wherein one or two carbons of said alkyl are optionally replaced by a heteroatom selected from O, S and N, and are optionally substituted 1 to 3 substituents selected from the group consisting of —C(O)$OR^6$, —$OR^6$, $C_1$–$C_{10}$ alkanoyl, halo, nitro, cyano, $R^6$, $R^8$, —$NR^6R^7$, —$SR^6$, —$SOR^6$, —$SO_2R^6$ and —$SO_2NR^6R^7$;

$R^5$ is H, —C(O)$R^8$ or $C_1$–$C_{18}$ alkanoyl, wherein in the alkyl portion of said alkanoyl one or two carbons optionally may be replaced by a heteroatom selected from O, S and N;

each $R^6$ and $R^7$ is independently selected from H and $C_1$–$C_{10}$ alkyl; and each $R^8$ is independently a 4–10 membered heterocycic or $C_6$–$C_{10}$ aryl, wherein said heterocycyclic and aryl groups are optionally substituted by 1 to 3 substituents independently selected from the group consisting of 4–10 membered heterocyclic, $C_6$–$C_{10}$ aryl, —NHC(O)$R^6$, —NHC(O)NR$^6$R$^7$, —C(O)OR$^6$, —OR$^6$, —C(O)$R^6$, halo, nitro, cyano, $R^6$, —NR$^6$R$^7$, —SR$^6$, —S(O)R$^6$, —SO$_2$R$^6$ and —SO$_2$NR$^6$R$^7$, which comprises treating a compound of the formula II

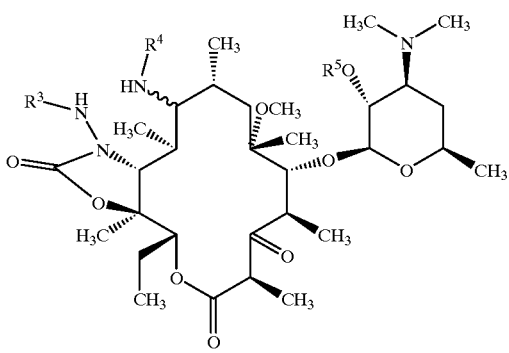

II wherein $R^3$, $R^4$ and $R^5$ are as defined above for the compound of formula I, with a compound of formula $R^1R^2C(O)$, wherein $R^1$ and $R^2$ are as defined above for the compound of formula I, in the presence of an acid.

Examples of suitable acids include acetic acid and para toluensulfonic acid (PTSA). For example, the compounds of formula I can be prepared in the presence of an acid acetic acid or PTSA (para-toluenesulfonic acid) in a solvent such as CHCl$_3$ or benzene, at a temperature within the range of about 40 to 80° C., for a period of about 1 to 20 hours. The preparation of formula II has been described in U.S. patent application Ser. No. 60/063676, filed Oct. 29, 1997, entitled "9-Amino-3-Keto Erythromycin Derivatives", (Yong-Jin Wu) and incorporpoated herein by reference in its entirety, and U.S. patent application Ser. No. 60/049,349, filed Jun. 11, 1997 and U.S. patent application Ser. No. 60/046,150, filed May 9, 1997, both are which are incorporated herein by reference in their entirety.

The term "treatment", as used herein, unless otherwise indicated, includes the treatment of prevention of a bacterial infection or protozoa infection as provided in the method of this invention.

Patients that can be treated with the compounds of formula I, and the pharmaceutically acceptable salts thereof, include mammals (particularly humans), fish, and birds suffering from infections caused by various microorganisms including Gram positive and Gram negative bacteria.

As used herein, unless otherwise indicated, the term "bacterial infection(s)" or "protozoa infections; includes bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include the following: pneumonia, otitis media, sinusitus, bronchitis, tonsillitis, and mastoiditis related to infection by *Streptococcus pneumoniae, Haemophilus influenzee, Moraxella catarrhalis, Staphylococcus aureus,* or Peptostreptococcus spp.; pharynigitis, rheumatic fever, and glomerulonephritis related to infection by *Streptococcus pyogenes,* Groups C and G streptococci, *Clostridium diptheriae,* or *Actinobacillus haemolyticum;* respiratory tract infections related to infection by *Mycoplasma pneumoniae, Legionella pneumophila, Streptococcus pneumoniae, Haemophilus influenzae,* or *Chlamydia pneumoniae;* uncomplicated skin and soft tissue infections, abscesses and osteomyelitis, and puerperal fever related to infection by *Staphylococcus aureus,* coagulase-positive staphylococci (i.e., *S. epidermidis, S. hemolyticus,* etc.), *Streptococcus pyogenes , Streptococcus agalactiae,* Streptococcal groups C–F (minute-colony streptococci), viridans streptococci, *Corynebacterium minutissimum,* Clostridium spp., or *Bartonella henselae;* uncomplicated acute urinary tract infections related to infection by *Staphylococcus saprophyticus* or Enterococcus spp.; urethritis and cervicitis; and sexually transmitted diseases related to infection by *Chiamydia trachomatis, Haemophilus ducreyi, Treponema pallidum, Ureaplasma urealyticum,* or *Neiserria gonorrheae;* toxin diseases related to infection by *S. aureus* (food poisoning and Toxic shock syndrome), or Groups A, B, and C streptococci; ulcers related to infection by *Helicobacter pylori;* systemic febrile syndromes related to infection by *Borrelia recurrentis;* Lyme disease related to infection by *Borrelia burgdorferi;* conjunctivitis, keratifis, and dacrocystitis related to infection by *Chiamydia trachomatis, Neisseria gonorrhoeae, S. aureus, S. pneumoniae, S. pyogenes, H. influenzae,* or Listeria spp.; disseminated *Mycobacterium avium* complex (MAC) disease related to infection by *Mycobacterium avium,* or *Mycobacterum intracellulare;* gastroenteritis related to infection by *Campylobacter jejune;* intestinal protozoa related to infection by Cryptosporidium spp.; odontogenic infection related to infection by viridans streptococci; persistent cough related to infection by *Bordetelia pertussis;* gas gangrene related to infection by *Clostridium perfringens* or Bacteroides spp.; and atherosclerosis related to infection by *Helicobacter pylori* or *Chiamydia pneumoniae.* Bacterial infections and protozoa infections and disorders related to such infections that may be treated or prevented in animals include the following: bovine respiratory disease related to infection by *P. haem., P. multocida, Mycoplasma bovis,* or Bordetelia spp.; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep. dysgalactiae,* Kiebsiella spp., Corynebacterium, or Enterococcus spp.; swine respiratory disease related to infection by *A. pleuro., P. multocida,* or Mycoplasma spp.; swine enteric disease related to infection by *E. coli, Lawsonia intracellularis,* Salmonella, or *Serpulina hyodyisinteriae;* cow footrot related to infection by Fusobacterium spp.; cow metritis related to infection by *E. coli;* cow hairy warts related to infection by *Fusobactefium necrophorum* or *Bacteroides nodosus;* cow pink-eye related to infection by

*Moraxella bovis*, cow premature abortion related to infection by protozoa (i.e. neosporium); urinary tract infection in dogs and cats related to infection by *E. coli;* skin and soft tissue infections in dogs and cats related to infection by *Staph. epidermidis, Staph. intermedius,* coagulase neg. Staph. or *P. multocida;* and dental or mouth infections in dogs and cats related to infection by Alcaligenes spp., Bacteroides spp., Clostridium spp., Enterobacter spp., Eubacterium, Peptostreptococcus, Pofphyromonas, or Prevotella. Other bacterial infections and protozoa infections and disorders related to such infections that may be treated or prevented in accord with the method of the present invention are referred to in J. P. Sanford et al., "The Sanford Guide To Antimicrobial Therapy," 26th Edition, (Antimicrobial Therapy, Inc., 1996).

In the chemical structures depicted herein, a wavy line indicates that the stereochemistry at the chiral center to which the wavy line is connected is either an R or S configuration where the wavy line is connected to a carbon atom. In the compound of formula I, the wavy line at position 10 of the macrolide ring indicates that the methyl group can be either R or S configuration at that position. In the compound of formula I, the wavy line connected to the oxime nitrogen at position 9 of the macrolide ring indicates that the —OR$^1$ moiety is in an E or Z configuration.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. Said alkyl group may include one or two double or triple bonds. It is understood that for cyclic moieties at least three carbon atoms are required in said alkyl group.

The term "alkanoyl", as used herein, unless otherwise indicated, includes —C(O)-alkyl groups wherein "alkyl" is as defined above.

The term "aryl", as used herein, unless otherwise indicated, includes an organic radical derived from an aromatic hydrocarbon by removal of one hydrogen, such as phenyl or naphthyl.

As used herein, unless otherwise indicated, "Ac" indicates an acetyl group.

As used herein, unless otherwise indicated, "Me" indicates a methyl group.

The term "4–10 membered heterocyclic", as used herein, unless otherwise indicated, includes aromatic and non-aromatic heterocyclic groups containing one or more heteroatoms each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indblinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyt, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The phrase "pharmaceutically acceptable salt(s)", as used herein, unless otherwise indicated, includes salts of acidic or basic groups which may be present in the compounds of formula I. The compounds of formula I that are basic in nature are capable of forming a wide variety of salts with various inorganic and organic acids. The acids that may be used to prepare pharmaceutically acceptable acid addition salts of such basic compounds of formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate i.e., 1,1'-methylene-bis-(2-hydroxy-3-naphthoate)] salts, Those compounds of the formula I that are acidic in nature, are capable of forming base salts with various pharmacologically acceptable cations. Examples of such salts include the alkali metal or alkaline earth metal salts and particularly, the sodium and potassium salts.

The present invention also includes all radiolabelled forms of the compounds of formula I, and pharmaceutically acceptable salts thereof, wherein the radiolabel is selected from $^3$H, $^{11}$C and $^{14}$C. Such radiolabelled compounds are useful as research or diagnostic tools.

Certain compounds of formula I may have asymmetric centers and therefore exist in different enantiomeric forms. This invention relates to the use of all optical isomers and stereoisomers of the compounds of formula I and mixtures thereof. In particular, the invention includes both the R and S configurations of the methyl group at C-10 of the macrolide ring of formula I, and both the E and Z configurations of the —OR$^1$ group connected to the nitrogen of the oxime moiety at C-9 of the macrolide ring of formula I. The compounds of formula I may also exist as tautomers. This invention relates to the use of all such tautomers and mixtures thereof.

DETAILED DESCRIPTION OF THE INVENTION

The preparation of the compounds of the present invention is illustrated in the following Schemes 1 to 3.

Scheme 1

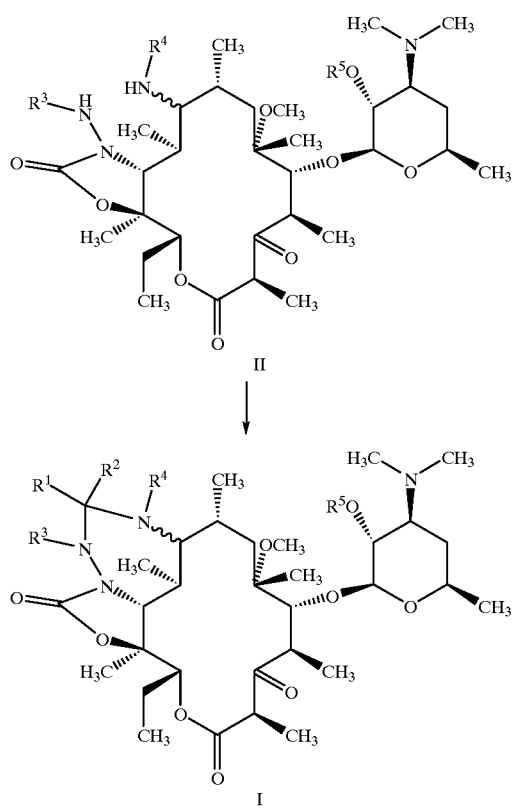

Scheme 2

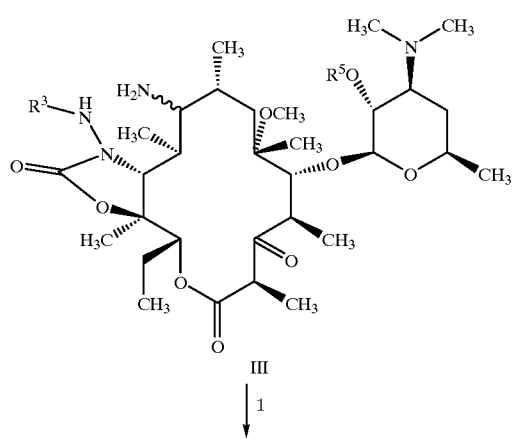

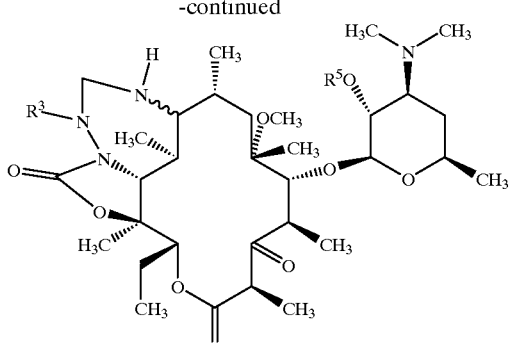

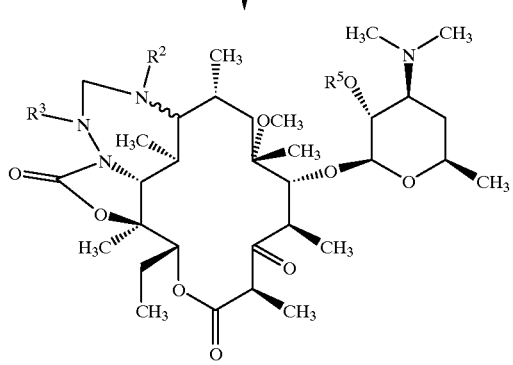

Scheme 3

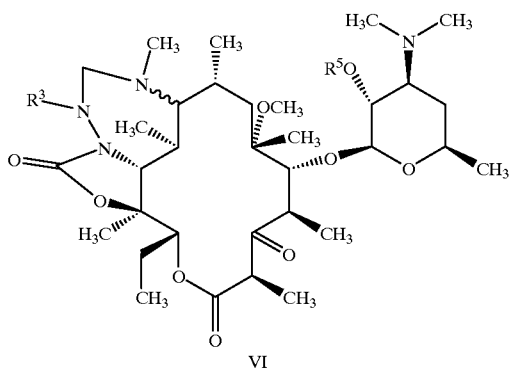

Scheme 1 illustrates the general synthesis of the compounds of the present invention. In Scheme 1, the starting compound of formula II can be prepared as described in U.S. patent application Ser. No. 60/063676, entitled "9-Amino-3-Keto Erythromycin Derivatives", (Yong-Jin Wu) filed Oct. 29, 1992. The compounds of formula I can be prepared by reacting the compound of formula II with $R^1R^2C=O$, wherein $R^1$ and $R^2$ are defined as above, in a solvent such as $CHCl_3$ or benzene, in the presence of an acid catalyst such as acetic acid or PTSA (para-toluenesulfonic acid) at a temperature within the range of about 40 to 80° C. for about 1 to 20 hours.

Scheme 2 illustrates the synthesis of the compounds of formula I, wherein $R^1$ and $R^2$ are hydrogens. The compounds of formula III can be prepared as described in U.S. patent application Ser. No. 60/063676, entitled "9-Amino-3-Keto Erythromycin Derivatives", *Yong-Jin Wu), filed Oct. 29, 1997. As shown in step I of scheme II, the compound of formula IV can be prepared from that of formula 3 by treatment with formaldehyde in a solvent such as $CHCl_3$ or benzene in the presence of an acid such as acetic acid at a temperature within the range of about 40 to 80° C. for about 1 to 20 hours. The secondary amine of formula IV can be transformed into tertiary amine of formula V, as shown in step 2 of scheme 2, through reductive alkylation.

Scheme 3 illustrates the synthesis of the compounds of formula I, wherein $R^1$ and $R^2$ are hydrogens, and $R^4$ is methyl. The synthesis of compounds of formula III is described in U.S. patent application Ser. No. 60/063676, entitled "9-Amino-3-Keto Erythromycin Derivatives", (Yong-Jin Wu), filed Oct. 29, 1997. The compound of formula VI can be prepared from compound of formula III, by reacting with formaldehyde and a reducing agent such as $NaBH_3CN$ or formic acid in the presence of an acid such as acetic acid in a solvent such as $CHCl_3$ or methanol at a temperature within the range of about 40 to 90° C. for about 4 to 40 hours.

The compounds of the present invention may have asymmetric carbon atoms. Such diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of formula I that are basic in nature are capable of forming a wide variety of different salts with various inorganic and organic acids. Although such salts must be pharmaceutically acceptable for administration to animals, it is often desirable in practice to initially isolate the compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the formula I that are acidic in nature, are capable of forming base salts with various pharmacologically acceptable cations. Examples of such salts include the alkali metal or alkaline-earth metal salts and particularly, the sodium and potassium salts. These salts may be prepared by conventional techniques. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The activity of the compounds of the present invention against bacterial and protozoa pathogens is demonstrated by the compound's ability to inhibit growth of defined strains of human (Assay I) or animal (Assays II and III) pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). The antibacterial assay is per-formed in microtiter trays and interpreted according to *Performance Standards for Antimicrobial Disk Susceptibility Tests—Sixth Edition; Approved Standard,* published by The National Committee for Clinical Laboratory Standards (NCCLS) guidelines; the minimum inhibitory concentration (MIC) is used to compare strains. acr AB or acr AB-like indicates that an intrinsia multidrug efflux pump exists in the strain. Compounds are initially dissolved in dimethylsulfoxide (DMSO) as 40 mg/ml stock solutions.

| Strain Designation | Macrolide Resistance Mechanism(s) |
| --- | --- |
| Staphylococcus aureus 1116 | susceptible parent |
| Staphylococcus aureus 1117 | ermB |
| Staphylococcus aureus 0052 | susceptible parent |
| Staphylococcus aureus 1120 | ermC |
| Staphylococcus aureus 1032 | msrA, mph, esterase |
| Staphylococcus hemolyticus 1006 | msrA, mph |
| Streptococcus pyogenes 0203 | susceptible parent |
| Streptococcus pyogenes 1079 | ermB |
| Streptococcus pyogenes 1062 | susceptible parent |
| Streptococcus pyogenes 1061 | ermB |
| Streptococcus pyogenes 1064 | mefA |
| Streptococcus agalactiae 1024 | susceptible parent |
| Streptococcus agalactiae 1023 | ermB |
| Streptococcus pneumoniae 1016 | susceptible |
| Streptococcus pneumoniae 1046 | ermB |
| Streptococcus pneumoniae 1095 | ermB |
| Streptococcus pneumoniae 1175 | mefE |
| Haemophilus influenzae 0085 | susceptible; acr AB-like |
| Haemophilus influenzae 0131 | susceptible; acr AB-like |
| Moraxella catarrhalis 0040 | susceptible |
| Moraxella catarrhalis 1055 | erythromycin intermediate resistance |
| Escherichia coli 0266 | susceptible; acr AB |
| Haemophilus influenzae 1100 | susceptible; acr AB-like |

Assay II is utilized to test for activity against *Pasteurella multocida* and Assay III is utilized to test for activity against *Pasteurella haemolytica.*

Assay II

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 μl of dimethylsulfoxide (DMSO). Dilutions of the test compound are prepared using uninoculated BHI broth. The concentrations of the test compound used range from 200 μg/ml to 0.098 μg/ml by two-fold serial dilutions. The *P. multocida* inoculated BHI is diluted with uninoculated BHI broth to make a $10^4$ cell suspension per 200 μl. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 μl of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 μl of the *P. haemolytica* culture is inoculated onto BHI agar plates containing the various concentrations of the test compound using a Steers Replicator and incubated for 18 hours at 37° C. Initial concentrations of the test compound range from 100–200 μg/ml. The MIC is equal to the concentration of the test compound exhibiting 100% inhibition of growth of *P. haemolytica* as determined by comparison with an uninoculated control.

The in vivo activity of the compounds of formula (I) can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3\times10^3$ CFU/ml bacterial suspension (*P. multocida* strain 59A006) intraperitoneally. Each experiment has at least 3 non-medicated control groups including one infected with 0.0× challenge dose and two infected with 1× challenge dose; a 10× challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge.

The $PD_{50}$ is a calculated dose at which the compound tested protects 50% of a group of mice from mortality due to the bacterial infection which would be lethal in the absence of drug treatment.

The compounds of formula I and their pharmaceutically acceptable salts (hereinafter referred to, collectively, as "the active compounds of this invention") may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the active compounds of this invention can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing an active compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art To implement the methods of this invention, an effective dose of an active compound of this invention is administered to a susceptible or infected animal (including mammals, fish and birds) by parenteral (intravenously, intramuscularly or subcutaneously), oral, or rectal routes, or locally as a topical application to the skin and/or mucous membranes. The route of administration will depend on the mammal, fish or bird that is being treated. The effective dose will vary with the severity of the disease, and the age, weight and condition of the animal. However, the daily dose will usually range from about 0.25 to about 150 mg/kg body weight of the patient to be treated, preferably from about 0.25 to about 25 mg/kg.

The Examples provided below illustrate specific embodiments of the invention, but the invention is not limited in scope to the Examples specifically exemplified.

EXAMPLE 1

9-deoxo-9-amino-11-deoxy-5-O-desosaminyl-11-(3-quinolin-4-yl-propyl)hydrazo-11b,9a-methylene-6-O-methyl-3-oxoerythronolide A, 11,12-carbamate (formula I, $R^1=R^2=R^4=R^5=H$, $R_3$=3-quinolin-4-yl-propyl)

To a solution of 9-deoxo-9-amino-11-deoxy-5-O-desosaminyl-11-(3-quinolin-4-yl-propyl)hydrazo-6-O-methyl-3-oxoerythronolide A, 11,12-carbamate (132 mg, 0.17 mmol), in $CHCl_3$ (10 mL) at room temperature was added 37% aqueous $CH_2O$ (0.13 mL, 1.73 mmol) followed by HOAc(0.12 mL, 12.7 mmol). The resulting solution was heated at reflux for 1 hour. Saturated $NaHCO_3$ was added followed by $CH_2Cl_2$, the organic layer was separated, and the aqueous layer was extracted with $CH_2Cl_2$. The combined organic layers were washed with brine, dried over $MgSO_4$, and concentrated. The residue was purified by preparative thin layer chromatography (TLC) (89% $CH_2Cl_2$-9% methanol-1% $NH_3.H_2O$) to afford the title compound as a white solid (106 mg).

Exact mass calculated for $C_{44}H_{68}N_5O_9$(M+H): 810.5017; found: 824.5016. MS: m/z 811 (M+H).

EXAMPLE 2

9-deoxo-9-amino-11-deoxy-5-O-desosaminyl-11-(3-quinolin-4-yl-propyl)hydrazo-11b,9a-methylene-9a-methyl6-O-methyl-3-oxoerythronolide A, 11,12-carbamate (formula I, $R^1=R^2=R^5=H$, $R^4$=methyl, $R_3$=3-quinolin-4-yl-propyl)

To a solution of 9-deoxo-9-amino-11-deoxy-5-O-desosaminyl-11-(3-quinolin-4-yl-propyl)hydrazo-6-O-methyl-3-oxoerythronolide A, 11,12-carbamate (18 mg, 0.02 mmol), in $CHCl_3$ (1 mL) at room temperature was added 37% aqueous $CH_2O$ (17 $\mu L$, 0.22 mmol) followed by $HCO_2H$(16 $\mu L$). The resulting solution was heated at reflux for 1 hour. Saturated $NaHCO_3$ was added followed by $CH_2Cl_2$, the organic layer was separated, and the aqueous layer was extracted with $CH_2Cl_2$. The combined organic layers were washed with brine, dried over $MgSO_4$, and concentrated. The residue was purified by preparative TLC (89% $CH_2Cl_2$-9% MeOH-1% $NH_3.H_2O$) to afford the title compound as a white solid (12 mg).

Exact mass calculated for $C_{45}H_{70}N_5O_9$ (M+H): 824.5174; found: 824.5157.

EXAMPLE 3

9deoxo-9-amino-11-deoxy-5-O-desosaminyl-11-(3-pyridin-4-yl-propyl)hydrazo-11b,9a-methylene-6-O-methyl-3-oxoerythronolide A, 11,12-carbamate (formula I, $R^1=R^2=R^4=R^5=H$, $R_3$=3-pyridin-4-yl-propyl)

To a solution of 9-deoxo-9-amino-11-deoxy-5-O-desosaminyl-11-(3-pyridin-4-yl-propyl)hydrazo-6-O-methyl-3-oxoerythronolide A, 11,12-carbamate (150 mg, 0.20 mmol), in $CHCl_3$ (6 mL) at room temperature was added 37% aqueous $CH_2O$ (0.14 mL, 2.0 mmol) followed by HOAc(0.14 mL, 2.4 mmol). The resulting solution was heated at reflux for 2 hours. Saturated $NaHCO_3$ was added followed by $CH_2Cl_2$, the organic layer was separated, and the aqueous layer was extracted with $CH_2Cl_2$. The combined organic layers were washed with brine, dried over $MgSO_4$, and concentrated. The residue was purified by preparative thin layer chromatography (TLC) (89% $CH_2Cl_2$-9% methanol-1% $NH_3.H_2O$) to afford the title compound as a white solid (46 mg).

MS: m/z 760 (M+H)

EXAMPLE 4

9-deoxo-9-amino-11-deoxy-5-O-desosaminyl-11-(3-pyridin-4-yl-propyl)hydrazo-11b,9a-methylene-9a-methyl-6-O-methyl-3-oxoerythronolide A, 11,12-carbamate (formula I, $R^1=R^2=R^5=H$, $R_3$=3-pyridin-4-yl-propyl, $R^4$=Me)

To a solution of 9-deoxo-9-amino-11-deoxy-5-O-desosaminyl-11-(3-pyndin-4-yl-propyl)hydrazo-6-O- methyl-3-oxoerythronolide A, 11,12-carbamate (110 mg, 0.15 mmol), in CHCl₃ (5 mL) at room temperature was added 37% aqueous CH₂O (0.10 mL, 1.5 mmol) followed by HCO₂H (68 uL, 1.5 mmol). The resulting solution was heated at reflux for 1.5 hours. Saturated NaHCO₃ was added followed by CH₂Cl₂, the organic layer was separated, and the aqueous layer was extracted with CH₂C₂. The combined organic layers were washed with brine, dried over MgSO₄, and concentrated. The residue was purified by preparative thin layer chromatography (TLC) (89% CH₂Cl₂-9% methanol-1% NH₃.H₂O) to afford the title compound as a white solid (65 mg).

MS: m/z 774 (M+H)

EXAMPLE 5

9-deoxo-9-amino-11-deoxy-5-O-desosaminyl-11-(3-(4-phenyl-imidazol-1-yl)-propyl)hydrazo-11b,9a-methylene-6-O-methyl-3oxoerythronolide A, 11,12-carbamate (formula I, $R^1=R^2=R^4=R^5=H$, $R^3=3$-(4-phenyl-imidazol-1-yl-propyl)

To a solution of 9-deoxo-9-amino-11-deoxy-5-O-desosaminyl-11-(3-(4-phenyl-imidazol-1-yl)-propyl) hydrazo-6-O-methyl-3-oxoerythronolide A, 11,12-carbamate (153 mg, 0.19 mmol), in CHCl₃ (4 mL) at room temperature was added 37% aqueous CH₂O(0.15 mL, 2.0 mmol) followed by HOAc (0.14 mL, 2.4 mmol). The resulting solution was heated at reflux for 1 hour. Saturated NaHCO₃ was added followed by CH₂Cl₂, the organic layer was separated, and the aqueous layer was extracted with CH₂Cl₂. The combined organic layers were washed with brine, dried over MgSO₄, and concentrated. The residue was purified by preparative thin layer chromatography (TLC) (89% CH₂Cl₂-9% methanol-1% NH₃.H₂O) to afford the title compound as a white solid (68 mg).

MS: m/z 825 (M+H)

EXAMPLE 6

9-deoxo-9-amino-11-deoxy-5-O-desosaminyl-11-(3-(4-phenyl-imidazol-1-yl)-propyl)hydrazo-11b,9a-methylene-9a-methyl-6-methyl-3-oxoerythronolide A, 11,12-carbamate (formula I, $R^1=R^2=R^5=H$, $R^3=$ 3-(4-phenyl-imidazol-1-yl)-propyl, $R^4=Me$)

To a solution of 9-deoxo-9-amino-11-deoxy-5-O-desosaminyl-11-(3-(4-phenyl-imidazol-1-yl)-propyl) hydrazo-6-O-methyl-3-oxoerythronolide A, 11,12-carbamate (700 mg, 0.86 mmol), in CHCl₃ (16 mL) at room temperature was added 37% aqueous CH₂O (0.64 mL, 8.6 mmol) followed by HCO₂H (0.4 mL, 10.3 mmol). The resulting solution was heated at reflux for 1.5 hours. Saturated NaHCO₃ was added followed by CH₂Cl₂, the organic layer was separated, and the aqueous layer was extracted with CH₂Cl₂. The combined organic layers were washed with brine, dried over MgSO₄, and concentrated. The residue was purified by preparative thin layer chromatography (TLC) (89% CH₂C₂-9% methanol-1% NH₃.H₂O) to afford the title compound as a white solid.

MS: m/z 839 (M+H)

EXAMPLE 7

9-deoxo-9-amino-11-deoxy-5-O-desosaminyl-11-(3-(4-pyridin-3-yl-imidazol-1-yl)-propyl)hydrazo-11b, 9a-methylene 6-O-methyl-3oxoerythronolide A, 11, 12-carbamate (formula I, $R^1=R^2=R^4=R^5=H$, $R^3=3$-(4-pyridin-3-yl-imidazol-1-yl)-propyl)

To a solution of 9-deoxo-9-amino-11-deoxy-5-O-desosaminyl-11-(3-(4-pyridin-3-yl-imidazol-1-yl)-propyl) hydrazo-6-O-methyl-3-oxoerythronolide A, 11,12-carbamate (50 mg, 0.06 mmol), in CHCl₃ (0.60 mL) at −78° C. was added 37% aqueous CH₂O (46 uL, 0.61 mmol)). The resulting solution was stirred at −78° C. for 1 hour. Saturated NaHCO₃ was added followed by CH₂Cl₂, the organic layer was separated, and the aqueous layer was extracted with CH₂Cl₂. The combined organic layers were washed with brine, dried over MgSO₄, and concentrated. The residue was purified by preparative thin layer chromatography (TLC) (89% CH₂Cl₂-9% methanol-1% NH₃.H₂O) to afford the title compound as a white solid (28 mg).

MS: m/z 826 (M+H)

EXAMPLE 8

9-deoxo-9-amino-11-deoxy-5-O-desosaminyl-11-(3-(benzotriazol-2yl)-propyl)hydrazo-11b,9a-methylene-6-O-methyl-3-oxoerythronolide A, 11, 12-carbamate (formula I, $R^1=R^2=R^5=H$, $R^4=Me$, $R^3=3$-(benzotriazol-2yl)-propyl)

To a solution of 9-deoxo-9-amino-11-deoxy-5-O-desosaminyl-11-(3-3-(benzotriazol-2yl)-propyl)hydrazo-6-O-methyl-3-oxoerythronolide A, 11,12-carbamate (120 mg, 0.15 mmol), in CHCl₃ (5.0 mL) at room temperature was added 37% aqueous CH₂O (104 uL, 1.5 mmol) and HCO₂H (68 uL, 1.8 mmol). The resulting solution was heated under reflux for 1.5 hours. Saturated NaHCO₃ was added followed by CH₂Cl₂, the organic layer was separated, and the aqueous layer was extracted with CH₂Cl₂. The combined organic layers were washed with brine, dried over MgSO₄, and concentrated. The residue was purified by preparative thin layer chromatography (TLC) (89% CH₂Cl₂-9% methanol-1% NH₃.H₂O) to afford the title compound as a white solid (50 mg).

MS: m/z 814 (M+H)

What is claimed is:

1. A compound of the formula I

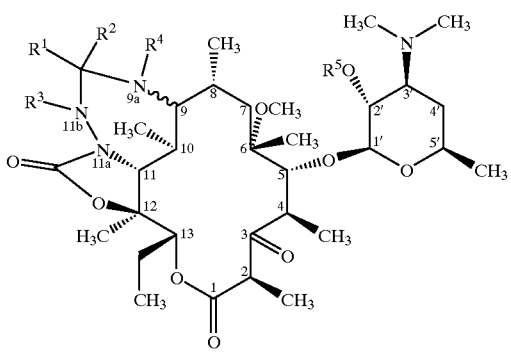

or a pharmaceutically acceptable salt thereof, wherein:
each $R^1$ and $R^2$ is independently selected from the group consisting of H and $C_1$–$C_{12}$ alkyl, wherein one or two carbons of said alkyl are optionally replaced by a heteroatom selected from the group consisting of O, S and N, and are optionally substituted by 1 to 3 substituents selected from the group consisting of —C(O)OR⁶, —OR⁶, $C_1$–$C_{10}$ alkanoyl, halo, nitro, cyano, R⁶, R⁸, —NR⁶R⁷, —SR⁶, —SOR⁶, —SO₂R⁶ and —SO₂NR⁶R⁷.

R³ is H, R⁷, C(O)R⁷, C(O)R⁸, C(O)OR⁷, C(O)OR⁸, or (CR⁶R⁷)$_m$R⁸, wherein m is an integer ranging from 0 to 6;

R⁴ is H or $C_1$–$C_{12}$ alkyl, wherein one or two carbons of said alkyl are optionally replaced by a heteroatom selected from the group consisting of O, S and N, and are optionally substituted by 1 to 3 substituents selected from the group consisting of —C(O)OR⁶, —OR⁶, $C_1$–$C_{10}$alkanoyl, halo, nitro, cyano, R⁶, R⁸, —NR⁶R⁷, —SR⁶, —SOR⁶, —SO₂R⁶ and —SO₂NR⁶R⁷;

R⁵ is H, —C(O)R⁸ or $C_1$–$C_{18}$ alkanoyl, wherein in the alkyl portion of said alkanoyl one or two carbons optionally may be replaced by a heteroatom selected from the group consisting of O, S and N;

each R⁶ and R⁷ is independently selected from the group consisting of H and $C_1$–$C_{12}$ alkyl; and each R⁸ is independently a 4–10 membered heterocyclic or $C_6$–$C_{10}$ aryl, wherein said heterocycyclic and aryl groups are optionally substituted 1 to 3 substituents independently selected from the group consisting of 4–10 membered heterocyclic, $C_6$–$C_{10}$ aryl, —NHC(O)R⁶, —NHC(O)NR⁶R⁷, —C(O)OR⁶, —OR⁶, —C(O)R⁶, halo, nitro, cyano, R⁶, —NR⁶R⁷, —SR⁶, —S(O)R⁶, —SO₂R⁶ and —SO₂NR⁶R⁷.

2. The compound of claim 1 wherein R⁵ is H.

3. The compound of claim 2 wherein R¹ is H.

4. The compound of claim 3 wherein R² is H.

5. The compound of claim 4 wherein R⁴ is H, methyl, ethyl, isopropyl, propyl, or cyclopropyl.

6. The compound of claim 1 wherein R³ is (CH₂)$_m$R⁸, m is an integer ranging from 0 to 6 and R⁸ is as defined in claim 1.

7. The compound of claim 6 wherein m is 3.

8. The compound of claims 6 wherein R⁸ is quinolin-4-yl, 4-phenyl-1-imidazol-1-yl, imidazo(4,5-b)pyridin-3-yl, or 4-pyridin-3-yl-imidazol-1-yl.

9. The compound of claim 1 selected from the group consisting of:

the compound of claim 1 wherein each of R¹, R², R⁴ and R⁵ is H and R³ is 3-quinolin-4-yl-propyl;

the compound of claim 1 wherein each of R¹, R² and R⁵ is H, R⁴ is methyl and R³ is 3-quinolin-4-yl-propyl;

the compound of claim 1 wherein each of R¹, R² and R⁵ is H, R⁴ is ethyl and R³ is 3-quinolin-4-yl-propyl;

the compound of claim 1 wherein each of R¹, R² and R⁵ is H, R⁴ is propyl and R³ is 3-quinolin-4-yl-propyl;

the compound of claim 1 wherein each of R¹, R² and R⁵ is H, R⁴ is isopropyl and R³ is 3-quinolin-4-yl-propyl;

the compound of claim 1 wherein each of R¹, R² and R⁵ is H, R⁴ is cyclopropyl and R³ is 3-quinolin-4-yl-propyl;

the compound of claim 1 wherein each of R¹, R², R⁴ and R⁵ is H and R³ is 3-(7-methoxy-quinolin-4-yl)-propyl;

the compound of claim 1 wherein each of R¹, R² and R⁵ is H, R⁴ is methyl and R³ is 3-(7-methoxy-quinolin-4-yl)-propyl;

the compound of claim 1 wherein each of R¹, R² and R⁵ is H, R⁴ is ethyl and R³ is 3-(7-methoxy-quinolin-4-yl)-propyl;

the compound of claim 1 wherein each of R¹, R² and R⁵ is H, R⁴ is propyl and R³ is 3-(7-methoxy-quinolin-4-yl)-propyl;

the compound of claim 1 wherein each of R¹, R² and R⁵ is H, R⁴ is isopropyl and R³ is 3-(7-methoxy-quinolin-4-yl)-propyl;

the compound of claim 1 wherein each of R¹, R² and R⁵ is H, R⁴ is cyclopropyl and R³ is 3-(7-methoxy-quinolin-4-yl)-propyl;

the compound of claim 1 wherein each of R¹, R², R⁴ and R⁵ is H and R³ is 3-(4-phenyl-imidazol-1-yl)-propyl;

the compound of claim 1 wherein each of R¹, R² and R⁵ is H, R⁴ is CH₃ and R³ is 3-(4-phenyl-imidazol-1-yl)-propyl;

the compound of claim 1 wherein each of R¹, R² and R⁵ is H, R⁴ is ethyl and R³ is 3-(4-phenyl-imidazol-1-yl)-propyl;

the compound of claim 1 wherein each of R¹, R² and R⁵ is H, R⁴ is propyl and R³ is 3-(4-phenyl-imidazol-1-yl)-propyl;

the compound of claim 1 wherein each of R¹, R² and R⁵ is H, R⁴ is isopropyl and R³ is 3-(4-phenyl-imidazol-1-yl)-propyl;

the compound of claim 1 wherein each of R¹, R² and R⁵ is H, R⁴ is cyclopropyl and R³ is 3-(4-phenyl-imidazol-1-yl)-propyl;

the compound of claim 1 wherein each of R¹, R², R⁴ and R⁵ is H and R³ is 3-(4-pyridin-3-yl-imidazol-1-yl)-propyl;

the compound of claim 1 wherein each of R¹, R² and R⁵ is H, R⁴ is CH₃ and R³ is 3-(4-pyridin-3-yl-imidazol-1-yl)-propyl;

the compound of claim 1 wherein each of R¹, R² and R⁵ is H, R⁴ is ethyl and R³ is 3-(4-pyridin-3-yl-imidazol-1-yl)-propyl;

the compound of claim 1 wherein each of R¹, R² and R⁵ is H, R⁴ is propyl and R³ is 3-(4-pyridin-3-yl-imidazol-1-yl)-propyl;

the compound of claim 1 wherein each of R¹, R² and R⁵ is H, R⁴ is isopropyl and R³ is 3-(4-pyridin-3-yl-imidazol-1-yl)-propyl;

the compound of claim 1 wherein each of R¹, R² and R⁵ is H, R⁴ is cyclopropyl and R³ is 3-(4-pyridin-3-yl-imidazol-1-yl)-propyl;

the compound of claim 1 wherein each of R¹, R², R⁴ and R⁵ is H and R³ is 3-imidazo(4,5 -b) pyridin-3-yl-propyl;

the compound of claim 1 wherein each of R¹, R² and R⁵ is H, R⁴ is CH₃ and R³ is 3-imidazo(4,5-b)pyridin-3-yl-propyl;

the compound of claim 1 wherein each of R¹, R² and R⁵ is H, R⁴ is ethyl and R³ is 3-imidazo(4,5-b)pyridin-3-yl-propyl;

the compound of claim 1 wherein each of R¹, R² and R⁵ is H, R⁴ is propyl and R³ is 3-imidazo(4,5-b)pyridin-3-yl-propyl;

the compound of claim 1 wherein each of R¹, R² and R⁵ is H, R⁴ is isopropyl and R³ is 3-imidazo(4,5-b)pyridin-3-yl-propyl;

the compound of claim 1 wherein each of R¹, R² and R⁵ is H, R⁴ is cyclopropyl and R³ is 3-imidazo(4,5-b)pyridin-3-yl-propyl;

the compound of claim 1 wherein each of R¹, R², R⁴ and R⁵ is H and R³ is 3-pyridin-4-yl-propyl; the compound of claim 1 wherein each of R¹, R² and R⁵ is H, R⁴ is CH₃ and R³ is 3-pyridin-4-yl-propyl;

the compound of claim 1 wherein each of R¹, R² and R⁵ is H, R⁴ is ethyl and R³ is 3-pyridin-4-yl-propyl;

the compound of claim 1 wherein each of R¹, R² and R⁵ is H, R⁴ is propyl and R³ is 3-pyridin-4-yl-propyl;

the compound of claim 1 wherein each of $R^1$, $R^2$ and $R^5$ is H, $R^4$ is isopropyl and $R^3$ is 3-pyridin-4-yl-propyl;

the compound of claim 1 wherein each of $R^1$, $R^2$ and $R^5$ is H, $R^4$ is cyclopropyl and $R^3$ is 3-pyridin-4-yl-propyl;

the compound of claim 1 wherein each of $R^1$, $R^2$, $R^4$ and $R^5$ is H and $R^3$ is 3-phenylpropyl;

the compound of claim 1 wherein each of $R^1$, $R^2$ and $R^5$ is H, $R^4$ is methyl and $R^3$ is 3-phenylpropyl;

the compound of claim 1 wherein each of $R^1$, $R^2$ and $R^5$ is H, $R^4$ is ethyl and $R^3$ is 3-phenylpropyl;

the compound of claim 1 wherein each of $R^1$, $R^2$ and $R^5$ is H, $R^4$ is propyl and $R^3$ is 3-phenylpropyl;

the compound of claim 1 wherein each of $R^1$, $R^2$ and $R^5$ is H, $R^4$ is isopropyl and $R^3$ is 3-phenylpropyl; and the pharmaceutically acceptable salts of the foregoing compounds.

10. A method of preparing a compound of the formula I

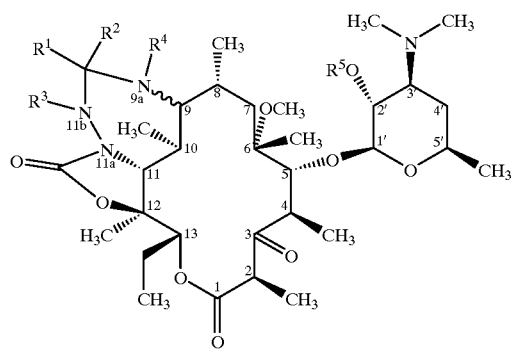

I or a pharmaceutically acceptable salt thereof, wherein:

each $R^1$ and $R^2$ is independently selected from the group consisting of H and $C_1$–$C_{12}$ alkyl, wherein one or two carbons of said alkyl are optionally replaced by a heteroatom selected from the group consisting of O, S and N, and are optionally substituted by 1 to 3 substituents selected from the group consisting of —C(O)OR$^6$, —OR$^6$, $C_1$–$C_{10}$ alkanoyl, halo, nitro, cyano, R$^6$, —NR$^6$R$^7$, —SR$^6$, —SOR$^6$, —SO$_2$R$^6$ and —SO$_2$NR$^6$R$^7$;

$R^3$ is H, $R^7$, C(O)R$^7$, C(O)R$^8$, C(O)OR$^7$, C(O)OR$^8$, or (CR$^6$R$^7$)$_m$R$^8$, wherein m is an integer ranging from 0 to 6;

$R^4$ is H or $C_1$–$C_{12}$ alkyl, wherein one or two carbons of said alkyl are optionally replaced by a heteroatom selected from the group consisting of O, S and N, and are optionally substituted 1 to 3 substituents selected from the group consisting of —C(O)OR$^6$, —OR$^6$, $C_1$–$C_{10}$ alkanoyl, halo, nitro, cyano, R$^6$, R$^8$, —NR$^6$R$^7$, —SR$^6$, —SOR$^6$, —SO$_2$R$^6$ and —SO$_2$NR$^6$R$^7$;

$R^5$ is H, —C(O)R$^8$ or $C_1$–$C_{18}$ alkanoyl, wherein in the alkyl portion of said alkanoyl one or two carbons optionally may be replaced by a heteroatom selected from the group consisting of O, S and N;

each $R^6$ and $R^7$ is independently selected from the group consisting of H and $C_1$–$C_{10}$ alkyl; and each $R^8$ is independently a 4–10 membered heterocyclic or $C_6$–$C_{10}$ aryl, wherein said heterocyclic and aryl groups are optionally substituted 1 to 3 substituents independently selected from the group consisting of 4–10 membered heterocyclic, $C_6$–$C_{10}$ aryl, —NHC(O)R$^6$, —NHC(O)NR$^6$R$^7$, —C(O)OR$^6$, —OR$^6$, —C(O)R$^6$, halo, nitro, cyano, R$^6$, —NR$^6$R$^7$, —SR$^6$, —S(O)R$^6$, —SO$_2$R$^6$ and —SO$_2$NR$^6$R$^7$, which comprises treating a compound of the formula II

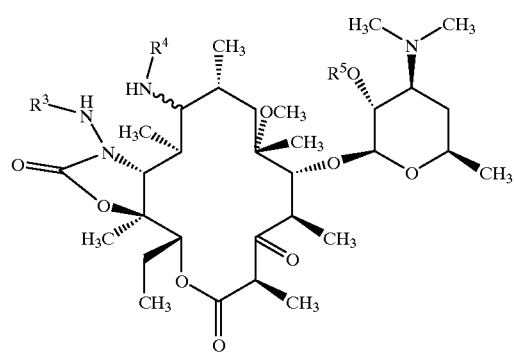

II wherein $R^3$, $R^4$ and $R^5$ are as defined above for the compound of formula I, with a compound of formula $R^1R^2C(O)$, wherein $R^1$ and $R^2$ are as defined above for the compound of formula I, in the presence of an acid.

11. The method of claim 10 wherein the acid is acetic acid.

12. The method of claim 10 wherein the acid is para-toluenesulfonic acid.

* * * * *